US008969012B2

(12) United States Patent
Tiwari

(10) Patent No.: US 8,969,012 B2
(45) Date of Patent: Mar. 3, 2015

(54) IMMUNOGENS FOR TREATMENT OF NEOPLASTIC AND INFECTIOUS DISEASE

(75) Inventor: Raj Tiwari, Bellerose, NY (US)

(73) Assignee: Applied Immune Technologies, Scarsdale, NY (US)

(*) Notice: Subject to any disclaimer, the term of this patent is extended or adjusted under 35 U.S.C. 154(b) by 0 days.

(21) Appl. No.: 13/341,671

(22) Filed: Dec. 30, 2011

(65) Prior Publication Data

US 2013/0183324 A1    Jul. 18, 2013

Related U.S. Application Data

(62) Division of application No. 10/379,462, filed on Mar. 3, 2003, now Pat. No. 8,088,569.

(60) Provisional application No. 60/360,720, filed on Mar. 1, 2002.

(51) Int. Cl.
| | | |
|---|---|---|
| *G01N 33/53* | (2006.01) | |
| *G01N 33/574* | (2006.01) | |
| *C12Q 1/70* | (2006.01) | |
| *C12N 15/10* | (2006.01) | |
| *A61K 39/00* | (2006.01) | |
| *C07K 16/30* | (2006.01) | |

(52) U.S. Cl.
CPC ........ *C12N 15/1037* (2013.01); *A61K 39/0011* (2013.01); *C07K 16/3069* (2013.01); *A61K 2039/6043* (2013.01); *A61K 2039/622* (2013.01); *C07K 2317/622* (2013.01)
USPC .................. 435/7.1; 435/5; 435/7.2; 435/7.23

(58) Field of Classification Search
CPC ........... C40B 30/00; A61K 2039/6043; A61K 39/0011; A61K 38/00; C07K 16/30; C07K 7/08; C07K 7/00
See application file for complete search history.

(56) References Cited

U.S. PATENT DOCUMENTS

| | | | | |
|---|---|---|---|---|
| 5,270,202 | A | * | 12/1993 | Raychaudhuri ............... 435/327 |
| 5,837,251 | A | | 11/1998 | Srivastava |
| 5,994,083 | A | * | 11/1999 | Felici et al. ..................... 435/7.1 |
| 6,139,841 | A | | 10/2000 | Srivastava |
| 6,187,312 | B1 | | 2/2001 | Srivastava |
| 6,235,280 | B1 | * | 5/2001 | Chatterjee et al. ......... 424/131.1 |
| 6,322,790 | B1 | | 11/2001 | Srivastava |
| 6,632,431 | B2 | * | 10/2003 | Wu ............................ 424/131.1 |
| 7,598,355 | B2 | * | 10/2009 | Nicchitta et al. ............. 530/413 |
| 2002/0037290 | A1 | * | 3/2002 | Armen ....................... 424/178.1 |
| 2009/0162405 | A1 | * | 6/2009 | Qian ........................... 424/277.1 |

FOREIGN PATENT DOCUMENTS

WO        00/38515 A1    7/2000

OTHER PUBLICATIONS

Arnold-Schild et al., Cancer Res., 2000, 60: 4175-4178.*
Kang et al., PNAS, 1991, 88: 4363-4366.*
Badithe et al., Proceedings of the American Association for Cancer Research Annual Meeting, Mar. 2001, vol. 42, pp. 680-681, 92nd Annual Meeting of the American Association for Cancer Research. New Orleans, LA, USA, Mar. 24-28, 2001.*
Arnold-Schild, D. et al., "One-Step Single-Chain Fv Recombinant Antibody-based Purification of gp96 for Vaccine Development", Cancer Res. (2000), vol. 60, pp. 4175-4178.
Brody, E. N. et al., "The Use of Aptamers in Large Arrays for Molecular Diagnostics" Molecular Diagnosis (1999), vol. 4:4, pp. 381-388.
Cepko, et al., "Construction and Applications of a Highly Transmissible Murine Retrovirus Shuttle Vector", Cell (1984), vol. 37, pp. 1053-1062.
Cho, C.Y. et al., "An Unnatural Biopolymer", Reports, Science (1993), vol. 261, pp. 1303-1305.
Cho, C.Y. et al., "Synthesis and Screening of Linear and Cyclic Oligocarbamate Libraries. Discovery for High Affinity Ligands for GPIIb/IIIa", J. Am. Chem. Soc. (1998), vol. 120 pp. 7706-7718.
Crystal, R.G., "Transfer of Genes to Humans: Early Lessons and Obstacles to Success", Science (1995), vol. 270:5235, pp. 404-410.
Houghten, R.A., "General method for the rapid solid-phase synthesis of large numbers of peptides: Specificity of antigen-antibody interaction at the level of individual amino acids", Proc. Natl. Acad. Sci. USA, vol. 82 (1985) pp. 5131-5135.
Jayasena, S.D., et al., "Aptamers: An Emerging Class of Molecules That Rival Antibodies in Diagnostics", Oak Ridge Conference, Clinical Chemistry (1999), vol. 45:9, pp. 1628-1650.
McCune et al., "Active Specific Immunotherapy with Tumor Cells and Corynebacterium Parvum A Phase I Study", Cancer (1979), vol. 43:5, pp. 1619-1623.
Nathalie, E.B. et al., "Heat Shock Protein-Peptide Complexes, Resconstructed in Vitro, Elicit Pepitide-specific Cytotoxic T Lymphocyte Response and Tumor Immunity", J. Exp. Med. (1997), vol. 186(8), pp. 1315-1322.
Panina-Bordignon et al, "Universally immunogenic T cell epitopes: promiscuous binding to human MHC class II and promiscuous recognition by T cells", European J. Immuno. (1989), vol. 19:12, pp. 2237-2242.
Rammensee et al., "MHC ligands and peptide motifs: first listing", Immunogenetics (1995), vol. 41, pp. 178-228.
Schumacher, T. N.M. et al.,"Identification of D-Peptide Ligands Through Mirror-Image Phage Display", Science (1996), vol. 271, pp. 3 1854-1857.
Simon R. J. et al., "Peptoids: A modular approach to drug discovery" Proc. Natl. Acad. Sci. USA (1992), vol. 89, pp. 9367-9371.
Thomas, C. E. et al., "Progress and Problems with the use of Viral Vectors for Gene Therapy", Nature Reviews Genetics (2003), vol. 4: pp. 346-358.

(Continued)

*Primary Examiner* — Hong Sang
(74) *Attorney, Agent, or Firm* — Kenyon & Kenyon LLP

(57) ABSTRACT

The present invention relates to prophylactic and therapeutic methods of immunization against neoplastic and infectious diseases. The invention provides a method for identification of novel immunogens and compositions of such immunogens that are useful for eliciting immune responses against antigens associated with neoplastic or infectious diseases.

23 Claims, 11 Drawing Sheets

(56) References Cited

OTHER PUBLICATIONS

Thompson, L. "Human Gene Therapy: Harsh Lessons, High Hopes", FDA Consumer Magazine, (Sep.-Oct. 2000), vol. 34:5, pp. 19-24.

Zuckermann, R.N., "Discovery of Nanomolar Ligands for 7-Transmembrane G-Protein-Coupled Receptors from a Diverse N-(Substituted) glycine Peptoid Library", J. Med. Chem., (1994), vol. 37, pp. 2678-2685.

\* cited by examiner

SEQUENCE LISTING

```
<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: synthetic peptide

<400> SEQUENCE: 1

Tyr Cys Gln Glu Gly Asp Ala Pro Arg Leu Cys Leu
1               5                   10

<210> SEQ ID NO 2
<211> LENGTH: 15
<212> TYPE: PRT
<213> ORGANISM: Artificial Sequence
<220> FEATURE:
<223> OTHER INFORMATION: synthetic peptide

<400> SEQUENCE: 2

Tyr Gln Pro Pro Ser Asp Ala Leu Arg Trp Ile Leu Arg Leu Gln
1               5                   10                  15

<210> SEQ ID NO 3
<211> LENGTH: 15
<212> TYPE: PRT
<213> ORGANISM: Artificial Sequence
```

-continued

```
<220> FEATURE:
<223> OTHER INFORMATION: synthetic peptide

<400> SEQUENCE: 3

Gly Gln Trp Gln Ser Gly Asp Arg Tyr Trp Met Glu Thr Ser Thr
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: synthetic peptide

<400> SEQUENCE: 4

Gly Lys Tyr Ile Arg Ser Val
1               5
```

IMMUNOGENS FOR TREATMENT OF NEOPLASTIC AND INFECTIOUS DISEASE

RELATED APPLICATIONS

This application is a divisional of U.S. Ser. No. 10/379,642, filed Mar. 3, 2003, now U.S. Pat. No. 8,088,569 issued Jan. 3, 2012, and claims priority to U.S. Ser. No. 60/360,720, filed Mar. 1, 2002, the contents of which applications are hereby incorporated by reference in their entireties.

FIELD OF THE INVENTION

The present invention relates to prophylactic and therapeutic methods of immunization against neoplastic and infectious diseases. More specifically, the invention provides a method for identification of novel immunogens and compositions of such immunogens that are useful for eliciting immune responses against antigens associated with neoplastic or infectious diseases.

BACKGROUND OF THE INVENTION

Therapy for neoplastic disease has largely involved the use of radiation, surgery and chemotherapeutic agents. However, these treatments, while beneficial in some cases, have marginal or no effect in many others. Furthermore, these approaches often have unacceptable toxicity. In cases where the cancer has become metastatic, there is often no effective curative treatment.

Specificity is a major problem with most anticancer agents. Ideally, anticancer agents would discriminate between host cells that are cancerous and host cells that are not cancerous. However, most anticancer drugs are indiscriminate at this level and generally target actively multiplying cells. Among the consequences are immunosuppression and disruption of hematopoiesis, epithelial tissues (e.g., intestinal mucosa) and the reproductive system.

Heat shock proteins (Hsps) were originally observed to be expressed in increased amounts in mammalian cells which were suddenly exposed to sudden elevations in temperature. Further experiments demonstrated that such proteins are produced in response to various types of stress, including, for example, glucose deprivation. The family of heat shock proteins further includes homologous proteins that are constitutively expressed. For example, whereas Hsp70 is not expressed at normal temperatures, a constitutively expressed heat shock protein cognate (Hsc70) participates in protein translocation across membranes and other functions. Most heat shock proteins are referred to as "molecular chaperones" in that they bind and stabilize proteins in their non-native states. For example, Hsps bind to nascent peptides emerging from ribosomes or extruded into the endoplasmic reticulum, at intermediate stages of folding, and assembly.

It has been observed that Hsps prepared from tumors in experimental animals are able to induce immune responses in a tumor specific manner. Evidence suggests that immunity is not conferred by the Hsp per se, but by peptides complexed with the Hsp.

Although autologous tumor-derived Hsp-peptide complexes are capable of eliciting an immune response against cells of the same tumor, there are drawbacks to use of such autologous complexes in vaccines for cancer treatment. For example, each patient would require a personalized or custom vaccine. To prepare such a vaccine, it would be necessary to provide Hsp preparations from a patients own tumor. Furthermore, ensuring availability of sufficient lisp preparations would necessitate culture of the tumor tissue are required and Hsp preparations from such tumors are low. Although peptides might be synthesized and complexed with Hsps in vitro, attempts to identify peptides of interest complexed with Hsps have generally been unsuccessful. Consequently, significant clinical constraints are imposed with regard to the manufacture of Hsp-peptide preparations.

SUMMARY OF THE INVENTION

A novel method is provided for identifying immunogens that can be used to treat or prevent a neoplastic or infectious disease. The method is particularly advantageous for identifying useful immunogens that can be used to elicit immune responses against target antigens associated with neoplastic or infectious diseases that are not immunogenic and that would otherwise escape immune surveillance. Immunogens identified by the method are administered to a patient in need of treatment for a neoplastic or infectious disease.

Accordingly, the invention provides a method of eliciting an immune response against a target cell in a host by isolating first binding substances that specifically bind to heat shock protein-peptide complexes differentially expressed by the target cell relative to a second cell, isolating second binding substances that specifically bind to the first binding substances, and immunizing the host with a therapeutically effective amount of the second binding substances. In various embodiments of the invention, the first and second binding substances can be mixtures of binding substances of a single species. In one embodiment, the binding substances can be obtained by screening libraries of phage displaying binding proteins such as antibody fragments or peptides. In another embodiment, the binding substances can be obtained by screening libraries of synthetic compounds.

The invention provides methods of obtaining binding substances that mimic peptides that are complexed with heat shock proteins in target cells. The peptide mimics ("mimotopes") are used as to immunize the host against the target cells. Target cells include, for example, neoplastic cells and infected cells.

The invention provides vaccines that incorporate the mimotopes. The mimotopes are incorporated by routine methods, such as covalent conjugation to earners and non-covalent binding to heat shock proteins.

The basis of the invention is a method for rapid identification of peptides or other molecules that contain mimotopes of target antigens differentially present on diseased cells. Advantageously, there is no requirement that any target antigen associated with the diseased cell be specifically known or identified.

According to the method, a first population of binding substances is screened to enrich or separate a subpopulation that binds to heat shock protein-peptide complexes obtained from a diseased cell or tissue and is relatively unreactive with heat shock protein-peptide complexes obtained from normal tissue. The first subpopulation can consist of multiple hsp-peptide complex-specific binding substances, or just one.

A second population of binding substances is then screened against the first subpopulation of binding substances to enrich or identify members of the second population that bind to the first subpopulation. The second subpopulation includes substances that both mimic epitopes present in the diseased cell or tissue and are immunologically active.

Thus, the second subpopulation of binding substances identified by the method comprises determinants which are useful for eliciting immune responses against antigens associated with the diseased cell or tissue. The antigens can be associated with neoplastic diseases or infectious agents. The peptides are particularly useful for eliciting immune responses against antigens which are otherwise unknown, poorly immunogenic, or to which a host is tolerized or becomes tolerized as a disease progresses.

Antigens which are poorly immunogenic include self antigens. An immune response directed against a self antigen can be particularly advantageous where the self antigen is displayed primarily or solely on tumor cells. Non-self antigens may also be poorly immunogenic where there is a high degree of similarity between the non-self antigen and a self antigen. The response against the non-self antigen may be inhibited by self-tolerance mechanisms. For example, the success of human papilloma virus (HPV) infection appears due in part to avoidance of the host's immune surveillance system that would otherwise respond to the foreign viral oncoproteins and stem the spread of HPV infection. The immune system avoidance is thought to be related to amino acid sequence similarity between HPV proteins and host proteins when evaluated on the size scale of peptides that can be presented by Class I or Class II MHC. In such cases, a method for eliciting immunity that avoids self-tolerance is useful.

Mimotope containing peptides identified by the invention are administered to subjects by methods that are well known in the art. In addition, the peptides can be administered by the usual routes in standard pharmaceutical compositions. The peptides can also be administered in mixtures and covalent or non-covalent complexes with heat shock proteins.

BRIEF DESCRIPTION OF THE DRAWINGS

FIG. 10 shows the effect of vaccination of synthetic peptides LX-8b or X15-7 on tumor progression.

DETAILED DESCRIPTION OF THE INVENTION

Figure 1:
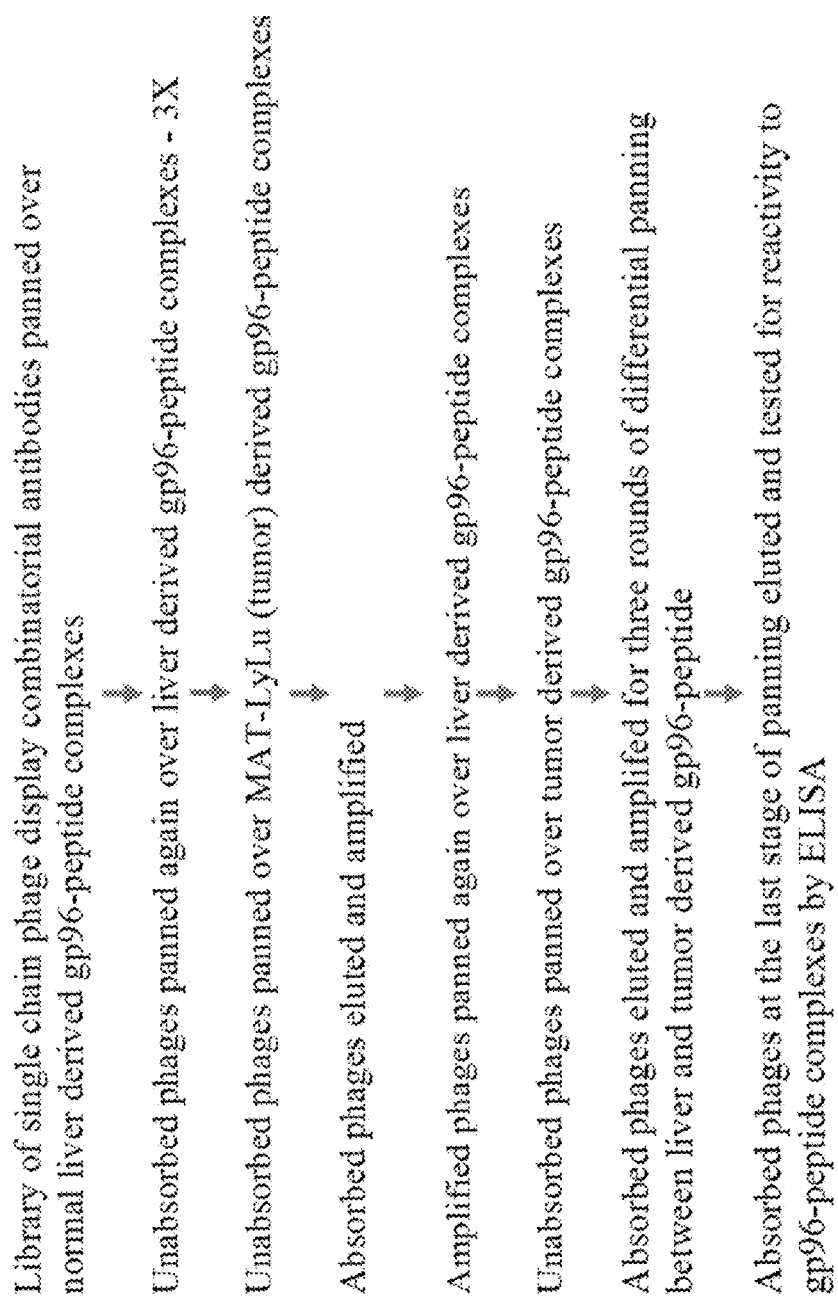
FIG. 1 shows a panning strategy for screening single chain antibodies (scFvs) that bind preferentially to gp96-peptide complexes from Mat-LyLu cells.
Figure 2:
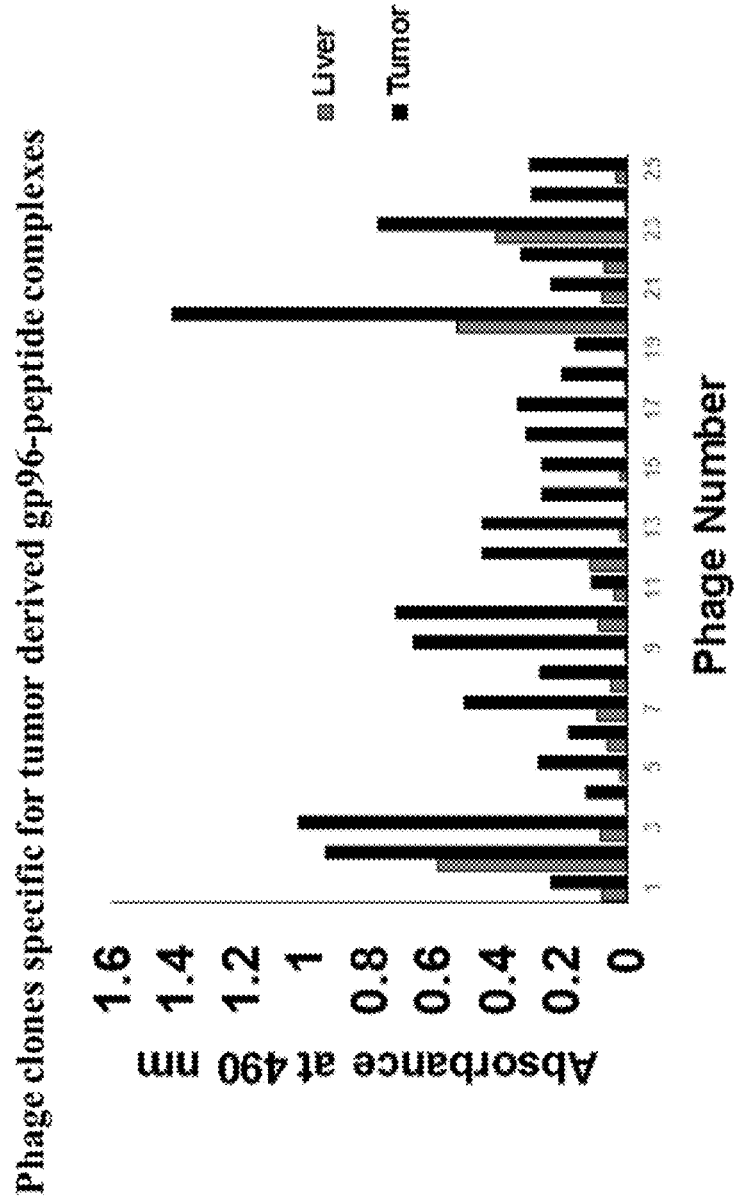
FIG. 2 shows a series of scFv-phage clones that are bind preferentially to gp96-peptide complexes from MAT-LyLu tumors from Copenhagen rats as compared to complexes isolated from tumor free tissue from the same animal.
Figure 3:
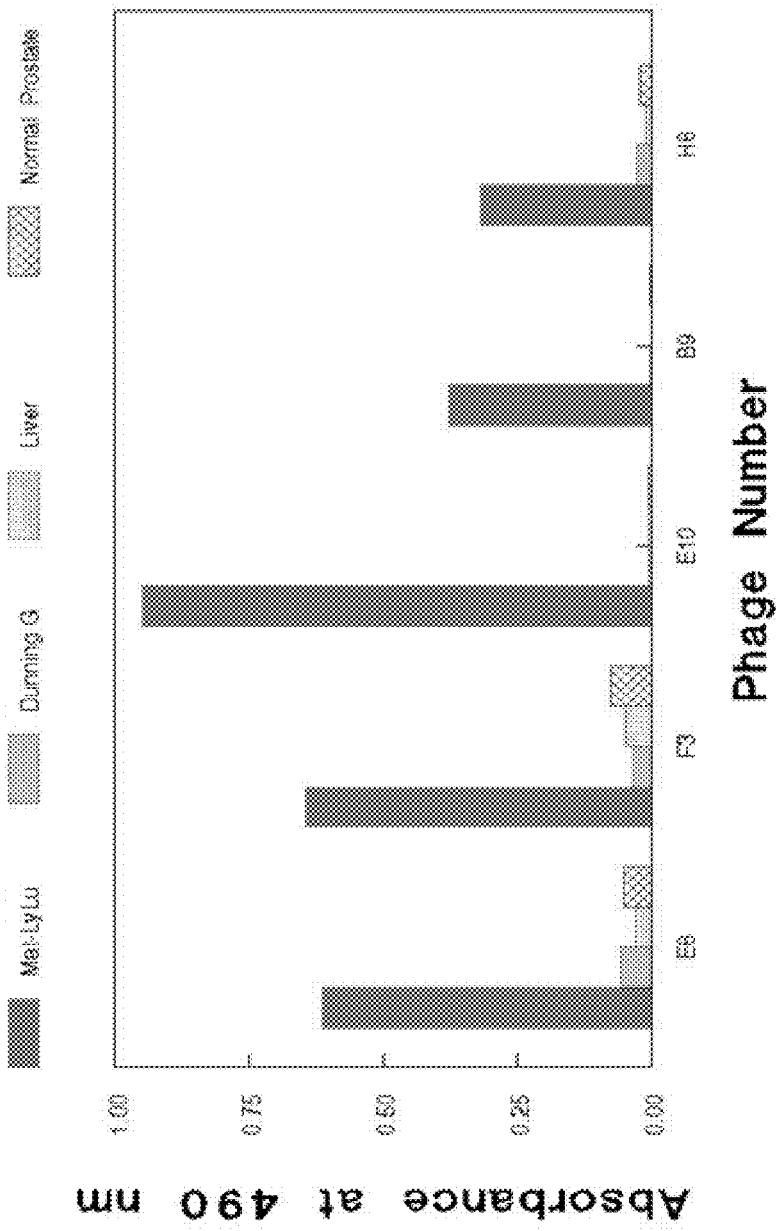
FIG. 3 shows the reactivity of five scFv antibodies with gp96-peptide complexes from MAT-LyLu cells as compared to normal tissue (liver, prostate) and a parental non-metastatic tumor line (Dunning G).
Figure 4:
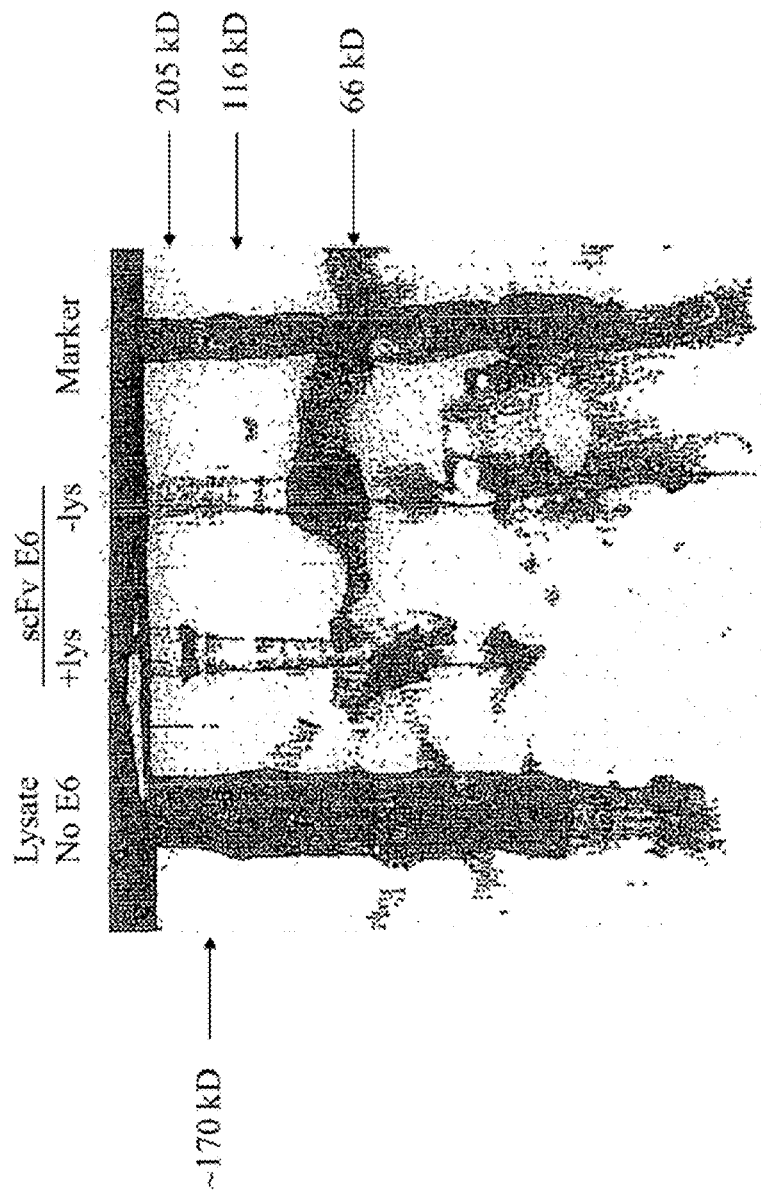
FIG. 4 shows a 170 kD protein precipitated from a MAT-LyLu cell lysate by scFv E6 (Lane 2) as compared to whole lysate (Lane 1) and scFv E6 alone (Lane 3).
Figure 5:
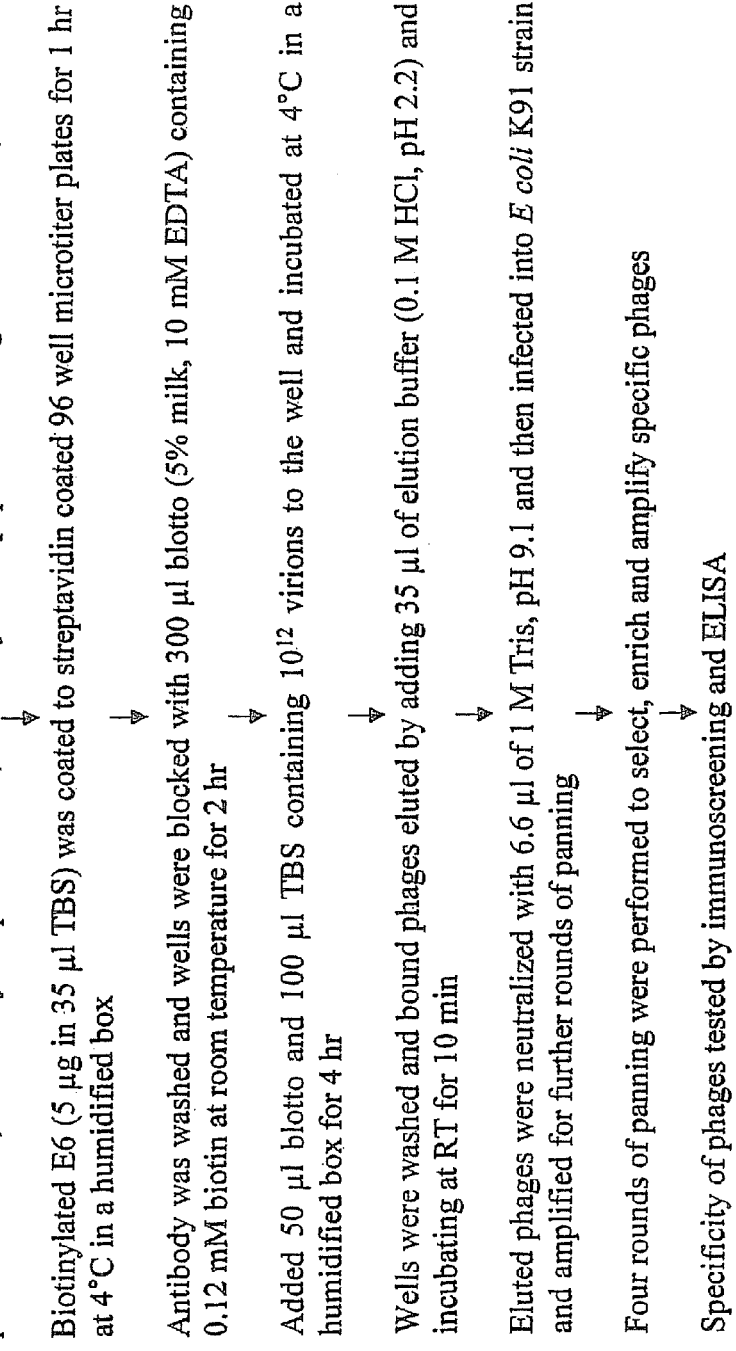
FIG. 5 shows a panning strategy for screening peptide mimics of the antigen that binds to scFv E6.
Figure 6:
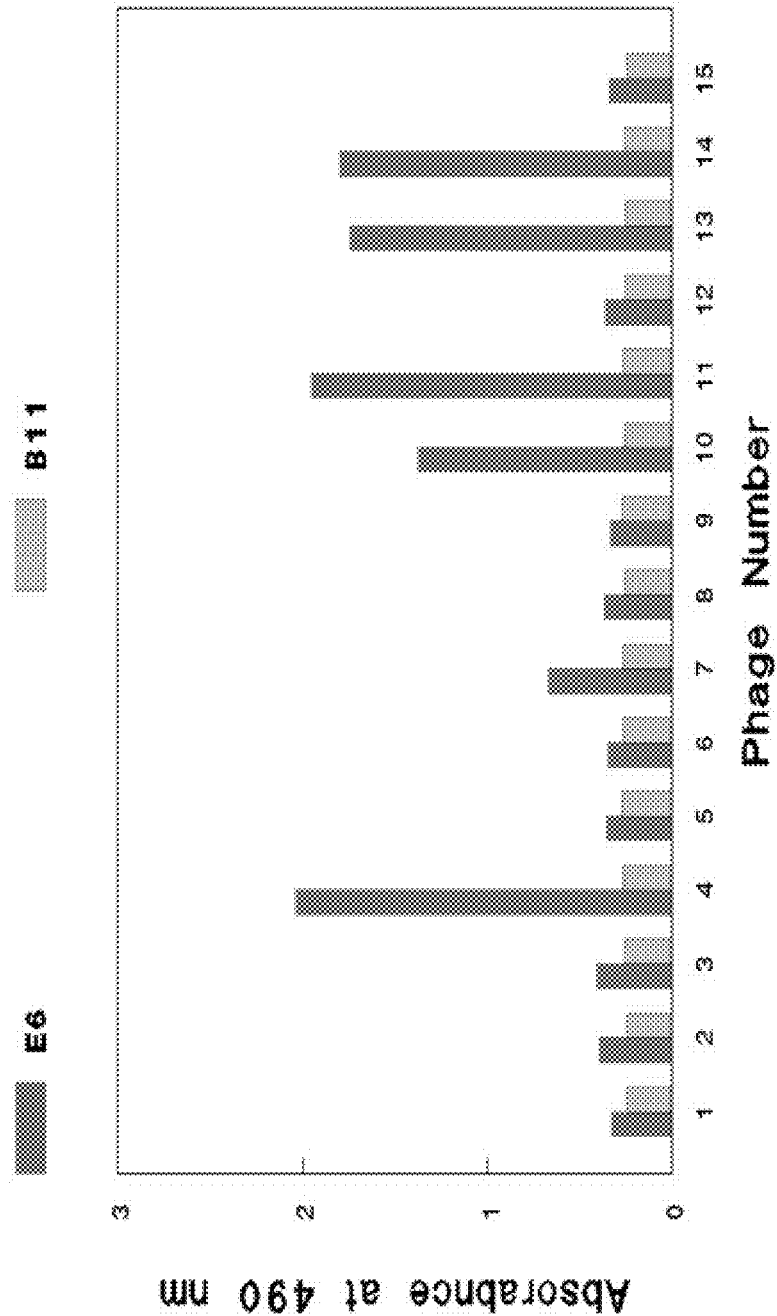
FIG. 6 shows reactivity with scFv E6 of peptide-phage isolated from a library displaying 15-mer peptides. B11 is a non-specific control scFv.
Figure 7:
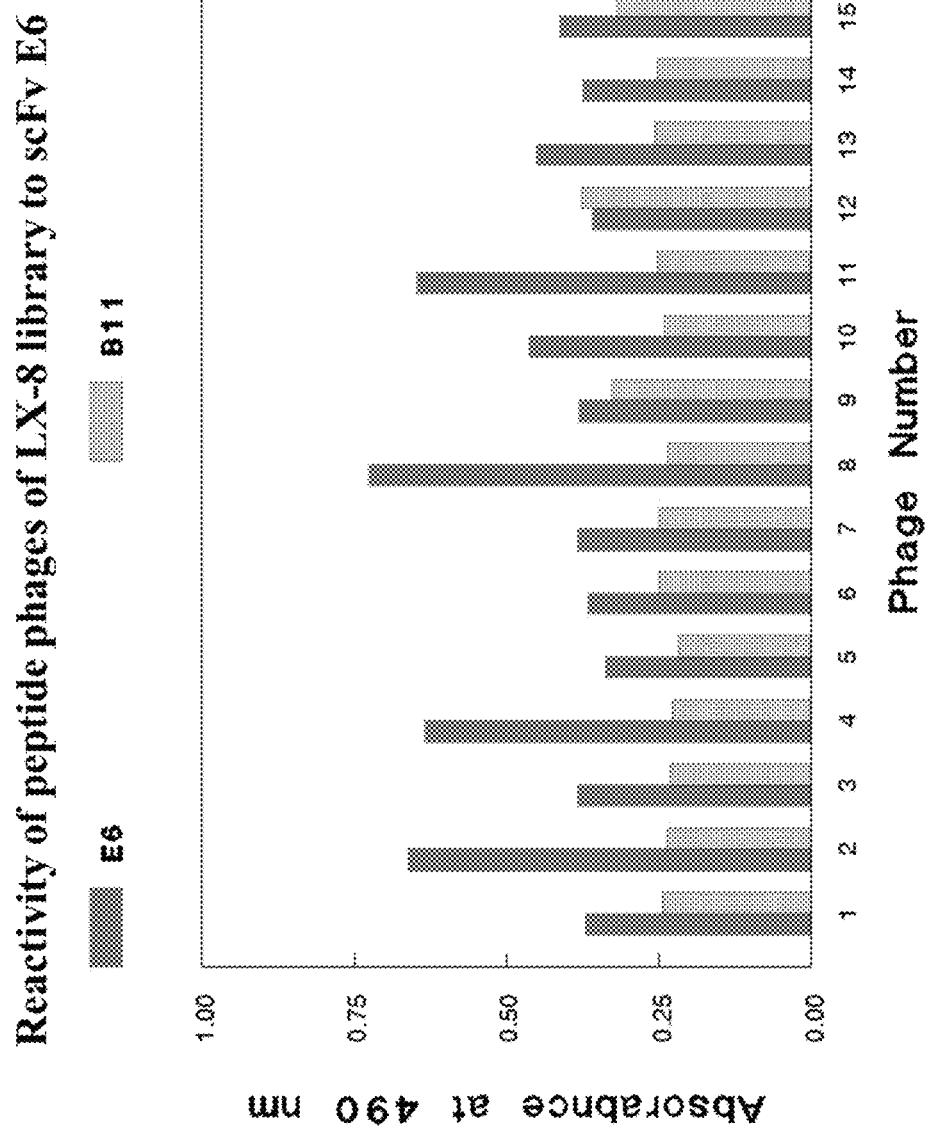
FIG. 7 shows the reactivity with scFv E6 of peptide-phage isolated from a library displaying 12-mer peptides containing a disulfide bridge. B11 is a non-specific control scFv.
Figure 8:
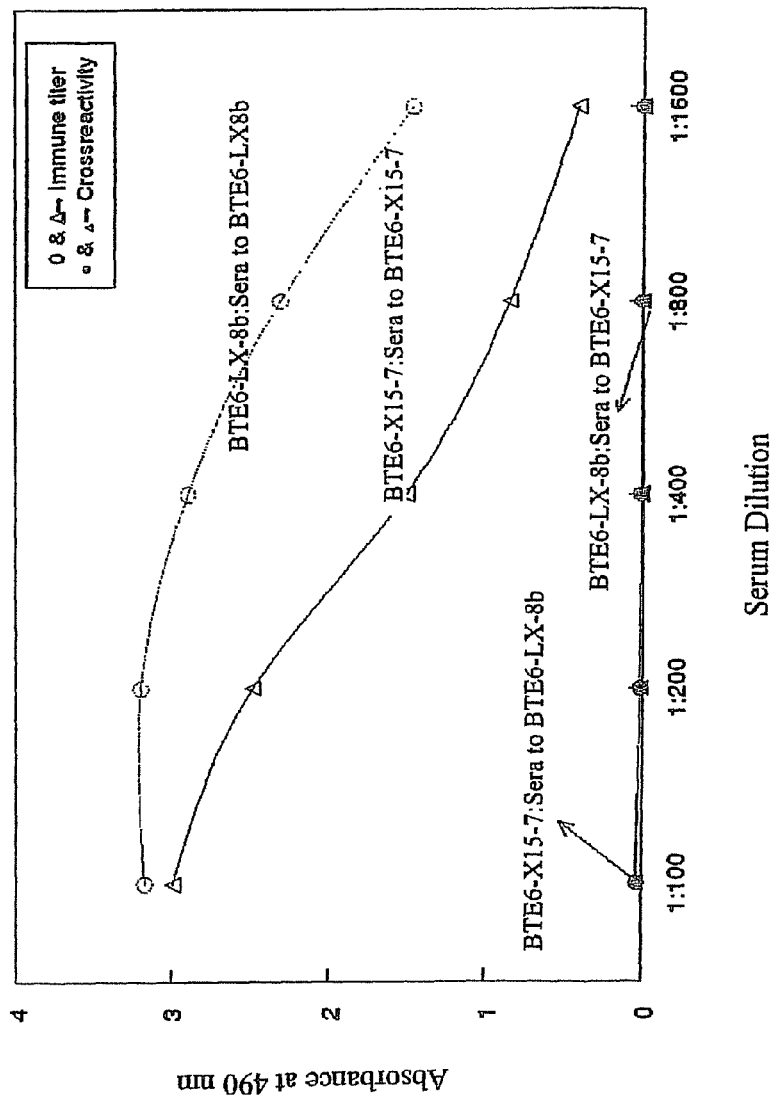
FIG. 8 shows immune reactivity of antisera from Copenhagen rats immunized with peptide LX-8 or X15-7. There is no apparent cross-reactivity with LX-8 of antisera from rats immunized with X15-7, or vice versa.
Figure 9A:
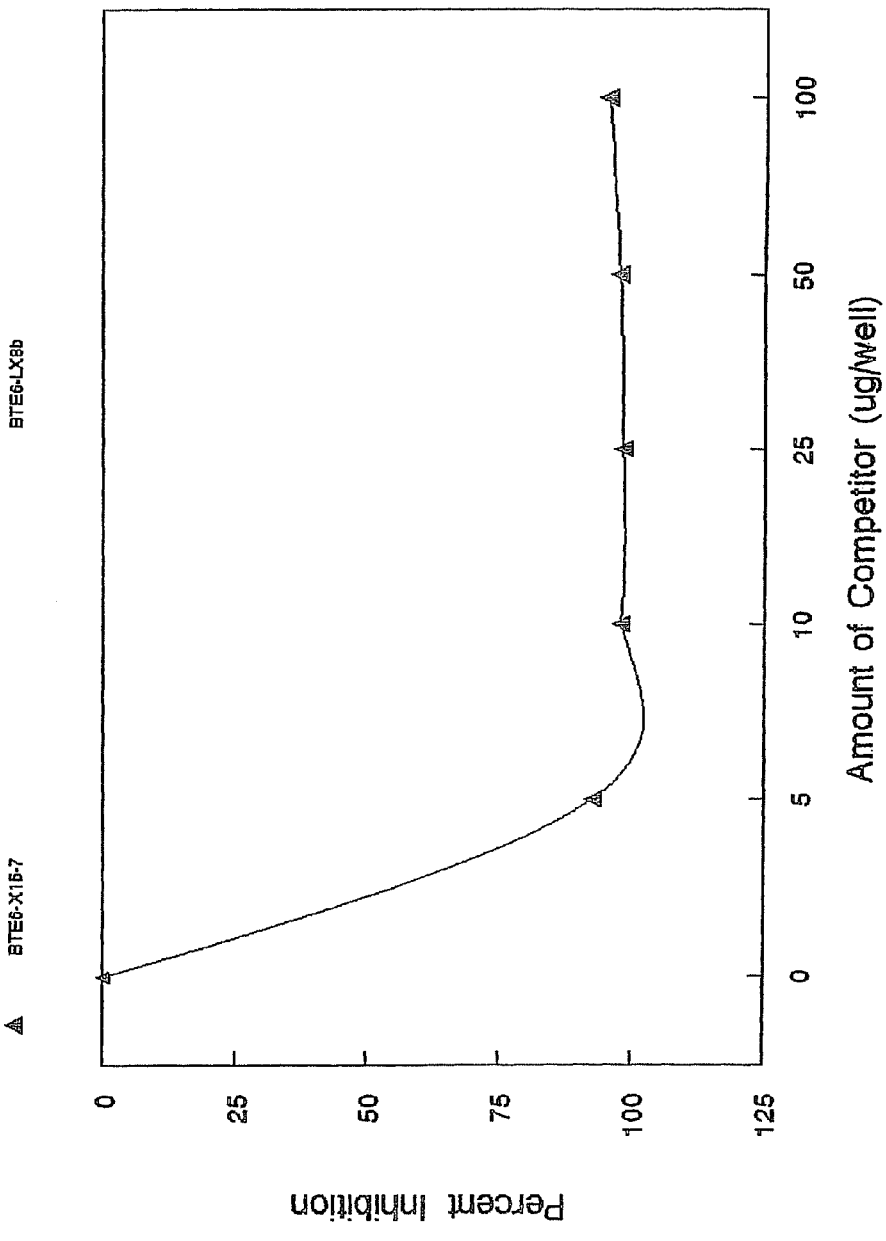
FIG. 9 shows binding inhibition by peptides LX-8 and X15-7 of binding of anti-E6-X15-7 to X15-7 (FIG. 9a) and anti-E6-LX-8 to LX-8 (FIG. 9b).
Figure 9B:
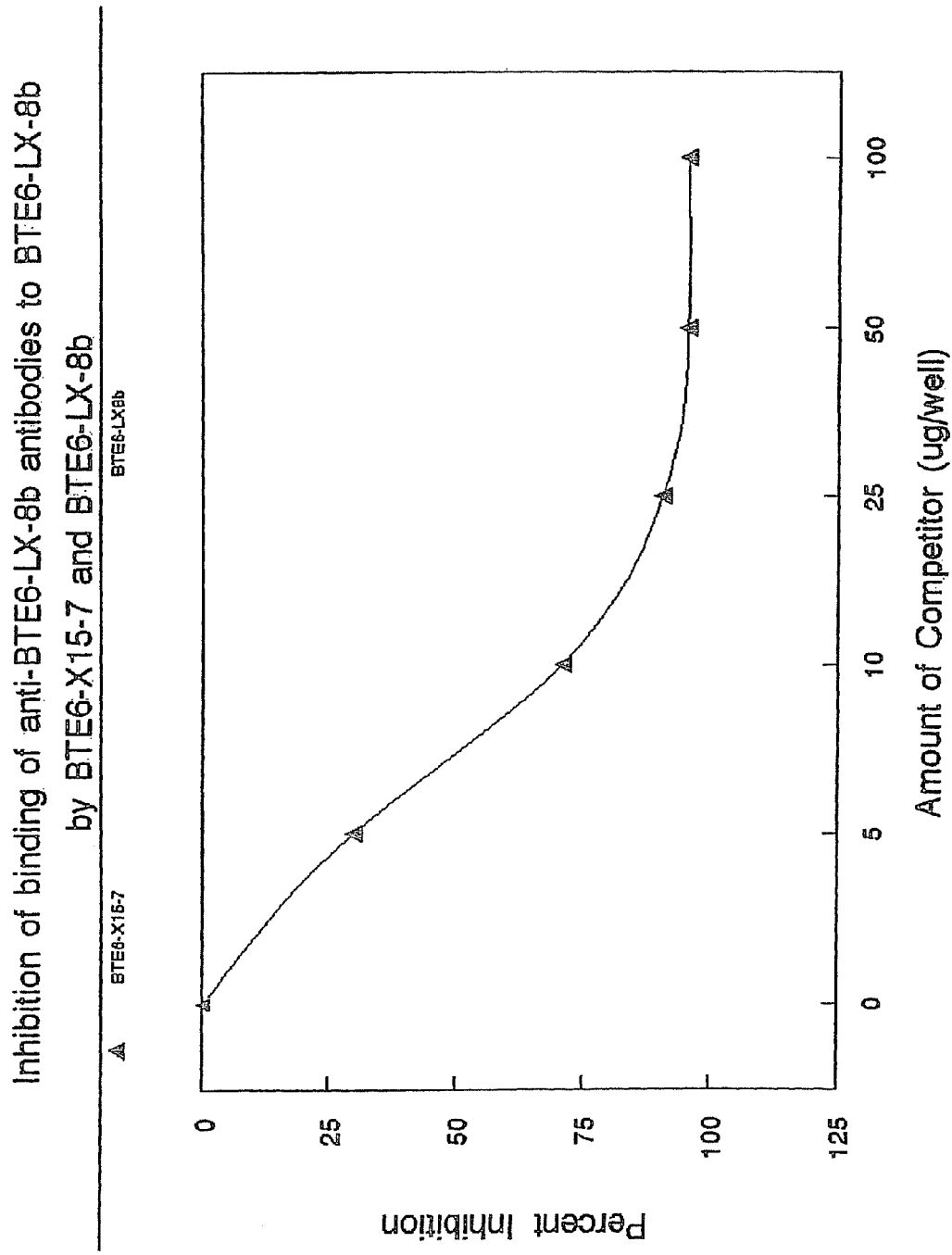

The present invention relates to substances and methods used to identify substances that are useful for inducing host immune responses against target antigens of interest, particularly cancer antigens and antigens from infectious agents that would be beneficial targets of a vigorous immune response, but that are poorly immunogenic. To overcome poor immunogenicity, the invention provides substances identified from libraries of epitope mimics that elicit active immune responses against the target antigen.

In an embodiment of the invention, candidate target antigens are peptides complexed with Hsps. As used herein, the term "heat shock protein" is used to encompass both proteins that are induced in response to stress conditions and homologs of such proteins that are constitutively expressed. Heat shock proteins of the invention include, but are not limited to gp96 (grp94), BiP (grp78), hsp70, hsc70, hsp60, hsp40, hsp90. In preferred embodiments, the heat shock protein is human.

The method is applicable to any cells or antigens of interest. Where an immune response against a target cell is desired, it is sufficient to select a target cell without further consideration for a particular expressed antigen. This is because the method allows for identification of mimotopes for any antigen that is differentially expressed by the target cell relative to a normal cell or control cell. Where mimotopes to a particular antigen are desired, a cell that expressed that antigen can be used. For example, a target cell can be engineered that expresses a target antigen of interest by transfecting and expressing a control cell line with a nucleic acid that encodes the target antigen of interest. Except for the target antigen of interest and any other proteins that my be expressed as a result of the presence of the target antigen in the cell, the target cell will express substantially the same proteins as the untransfected control cell.

The method is particularly useful for targeting diseased cells (e.g., neoplastic cells, infected cells) that express antigens which are expressed in lower amounts or not at all in other tissue. Examples of target cells include cells from a neoplastic disease, including but not limited to a sarcoma, a lymphoma, a leukemia, or a carcinoma, and in particular, with melanoma, carcinoma of the breast, carcinoma of the prostate, ovarian carcinoma, carcinoma of the cervix, colon carcinoma, carcinoma of the lung, glioblastoma, astrocytoma, etc. Alternatively, the target cell can be infected by, for example, a virus, a mycoplasma, a parasite, a protozoan, a prion and the like.

Target antigens of particular interest are those associated with, derived from, or predicted to be associated with a diseased cell such as a neoplastic or infected cell. Accordingly, target antigens can be from, for example, a human papilloma virus (see below), a herpes virus such as herpes simplex or herpes zoster, a retrovirus such as human immunodeficiency virus 1 or 2, a hepatitis virus, an influenza virus, a rhinovirus, respiratory syncytial virus, cytomegalovirus, adenovirus, *Mycoplasma pneumoniae*, a bacterium of the genus *Salmonella, Staphylococcus, Streptococcus, Enterococcus, Clostridium, Escherichia, Klebsiella, Vibrio, Mycobacterium*, amoeba, a malarial parasite, *Trypanosoma cruzi*, etc. In addition to tumor antigens and antigens of infectious agents, mutations of tumor suppressor gene products such as p53, or oncogene products such as Ras may also provide target antigens to be used according to the invention. The target antigen can be a self antigen, for example one associated with a cancer or neoplastic disease.

Generally, target antigens of the invention are present in diseased cells or tissue, but not in normal cells or tissue. However, it will be recognized that certain target antigens may be expressed in normal tissue in, for example a developmental or gender specific manner. For example, a host may be tolerized to a self-antigen that normally is expressed at an early stage of development. When that antigen is aberrantly expressed at another point in time, it can be an ideal target antigen. In another example, a target antigen of interest may be present in normal tissue of one sex, but not the other. This method further applies where a target antigen is expressed in diseased tissue, but normal tissue of the same cell type has been removed from the host. For example, following prostatectomy, any prostate specific protein is a potential target antigen for eliciting an immune response directed against metastatic cells from a prostate cancer, because normal host tissue that would be targeted by the immune response has already been removed. The invention is also applicable where a target antigen is expressed in relatively large amounts in diseased cells, and small amounts in normal cells. Here, an the intent is to elicit an immune response that is effective against cells expressing the target antigen in large amounts (e.g., having a dense population of a cell surface antigen), but that has little or no effect on cells expressing the target antigen in small amounts.

In an embodiment of the invention, binding substances are identified that are specific for hsp-peptide complexes from diseased cells or tissue. Binding substances include any synthetic and naturally occurring molecules that are specific for hsp-antigen complexes from the diseased cells or tissue. Examples include proteins, fragments thereof, polypeptides, polynucleotides, and synthetic analogs. Because the binding substances are simply a source of "binding sites," there is no requirement that the sequences be derived from a natural source, or that the structures resemble any naturally occurring protein. Synthetic analogs include, for existence, polypeptide- and polynucleotide-like polymers having modified backbones, side chains, and/or bases. In a preferred embodiment, the binding substances are antibodies and antibody-like molecules. Antibodies include complete immunoglobulins and fragments thereof that retain specific binding characteristics. Antibody fragments include, e.g., Fabs, Fvs, and scFvs. Antibody-like molecules include, e.g., molecules comprising Ig-like domains such as T cell receptors and the like. The antibodies can be classical monoclonal antibodies developed by cell fusion techniques, and screened for differential binding to disease-associated hsp-peptide complexes. Alternatively the antibodies can be populations of polyclonal antibodies raised against hsp-peptide complexes from diseased cells. Prior to use, such populations would be pre-bound to hsp-peptide complexes from normal tissue to remove components that are not disease specific.

In a preferred embodiment, synthetic antibody libraries are employed. A particularly preferred method for making and screening synthetic libraries is phage display, which conveniently allows for positive and negative screening steps and amplification of elements between screening steps. It is noted that any sort of binding substance can be used Antibody libraries are generally screened by a method that enriches for elements that bind to disease specific targets, and removes elements that bind to targets present in normal tissue. It is characteristic of phage display technology that enrichment is enhanced by repetition of screening steps. Thus, in certain embodiments of the invention, multiple rounds of positive and negative screens are performed. The number of rounds depends on the desired binding substances. Where a single binding substance is desired, the screening process is essentially complete when that substance is identified. Where a diverse population of binding proteins is desired, for example, where multiple target antigens exist, it is beneficial to repeat screening steps until a substantial proportion of the binding proteins are disease specific. Generally, at least half of the binding proteins will be disease specific. Preferably, at least 80% of the binding proteins will be disease specific. More preferably, at least 90% will be disease specific.

Immunogenic substances of the invention are identified by their ability to bind specifically to the above described binding substances. Immunogenic substances are generally identified by generating libraries and screening for desired binding characteristics. Preferred immunogenic substances of the invention are peptides, but the methods and examples disclosed are generally applicable to any epitope library. In an embodiment of the invention, peptides to be screened are encoded by filamentous phage and expressed as part of a phage coat protein. The technique of phage display is well known in the art, and allows for amplification of the library in between rounds of screening.

Peptides screened and identified by the method can be relatively short, and are generally 30 amino acids or less. Immunogenic substances are large enough to comprise a single T cell or B cell epitope. Peptide immunogens are preferable from 4 to 20 amino acids, and more preferably from 7 to 15 amino acids. The peptides can have flexible or constrained secondary structures. The flexibility of linear peptides is constrained, for example, by incorporation of proline or by disulfide bonds formed between cysteine residues.

Other types of libraries may also be employed, for example, any sort of synthetic polymers that can be screened and optionally, their structure or sequence determined. Numerous methods have been devised for generation of chemical diversity and mass screening of libraries. To simplify identification of library elements of interest, many libraries have the feature that synthesis steps are encoded. For example, in phage display, the displayed peptide is encoded in the genome encapsulated by the phage particle. Amino acid sequences of peptides identified by screening procedures are easily determined by sequencing a small predetermined part of the genome.

In another example, it has been demonstrated that peptides can be generated in numbers several orders of magnitude greater than by conventional one-at-a-time methods by synthesis on polyethylene rods or pins, arranged, for example, in a microtiter plate format. The pin technology is representative of techniques that generate libraries of single compounds in a spatially-differentiated manner. An alternative approach, to rapidly prepare large mixtures of compounds, is the split-pool approach (e.g., Houghten, R. A., 1985, *Proc. Natl. Acad. Sci. U.S.A.* 82:5131-5135) where a solid support material (e.g., beads) is physically segregated into equal portions for coupling to each of the individual initial reactants. This affords uniform coupling since competition between reactants is eliminated. The individual polymers are combined in a single vessel for washing and deprotection and then divided again into individual portions for, the next coupling. Using this approach, a complete set of possible molecular combinations is rapidly prepared in approximately equimolar amounts. Coincident with coupling reactions, "identifier" tags can be attached to the solid support material. The structure of the molecule on any bead identified through screening is obtained by decoding the identifier tags. Numerous methods of tagging the beads have now been reported.

Alternatives to peptide libraries include production of polymers of peptide-like and small organic molecules. For example, peptide libraries are a collection of N-substituted glycines as peptide monomers which are assembled in a modular fashion. (Zuckermann, R. N. et al, 1994, *J. Med. Chem.* 37:2678-2685.) The structures of the resulting compounds are unique, display unique binding properties, and incorporate the important functionalities of peptides in a novel backbone. Furthermore, studies suggest this class of compounds is resistant to enzymatic breakdown.

Thus, the invention can be practiced in a variety of ways. In a first non-limiting example of the invention, a single binding protein is identified that differentially binds to a hsp-peptide complex from a diseased cell. The binding protein is used to identify mimotope-containing peptide immunogens, and one of those peptide immunogens is selected for use in a treatment regimen. In a second example, a single binding protein is identified, but of the mimotope-containing peptide immunogens that are recovered, all or a multiplicity or the peptides are selected for treatment. In a third example, multiple binding proteins are identified and then used to obtain mimotope-containing peptides. It may be advantageous to further characterize the binding proteins and mimotope-containing peptides (e.g., to obtain amino acid sequence information), but further characterization is not critical to practice of the invention.

It is expected that individual mimotope-containing peptides will exhibit different degrees of immunogenicity. Immunogenicity can depend, for example, on the degree of sequence similarity between the peptide and the host proteome. Sequence similarity is easily determined by methods that are well known in the art. Immunogenicity can also depend on the genetic makeup of the host. For example, a variety of MHC alleles are present in the human population, and differences in peptide presentation to the immune system are observed depending on the MHC allele and the sequence of the peptide. Such differences in peptide presentation affect both the strength and the type of immune response (e.g., humoral, cell mediated, cytolytic). Databases and analysis methods have been developed that disclose sequence preferences of Class I and Class II MHC alleles and are well known to those of skill in the art. See, e.g., Rammensee et al., *Immunogenetics* 41:178-223 (1995).

In a preferred embodiment, peptide immunogens of the invention are conjugated to immunogenic carriers. As used herein, "immunogenic carrier" means a molecule which can assist T lymphocyte activation and helper T cell participation. Hence, to stimulate an immune response against an a peptide immunogen, the peptide can be covalently linked (i.e., conjugated) to such an immunogenic carrier. An immunogenic carrier of the invention can be a protein or portion of a protein which stimulates or enhances the immune response of the subject. Examples of immunogenic carrier proteins are KLH and BSA. Immunogenic carriers also include polypeptides that are promiscuous Class II activators (see, e.g., Panina-Bordignon et al., 1989). Conjugate linkages are made by methods well known to those of skill in the art.

In addition to immunogenic proteins and polypeptides which comprise a T cell epitope, carriers can also be constructs to which other immunogenic moieties (e.g., cytokines, polypeptides bearing T cell epitopes, etc.) can be linked. Branched constructs such as lipo-thioester and branched polylysine allow for multiple covalent linkages of such immunogenic moieties as well as conjugation of multiple polysialic acid polymers. Carriers further include proteins and polypeptides which have been modified by the covalent addition of immunogenically active moieties. Alternatively, the peptide immunogens can be incorporated into longer sequences of amino acids. The additional sequences can, for example, confer a desired function, such as the ability to bind to a heat shock protein. In certain embodiments, tandem arrays will be produced that comprise multiple copies of one peptide immunogen or comprise multiple peptide immunogens.

Immunogen-carrier conjugates are typically formulated with the adjuvants, which generally promote nonspecific immune responses. While commercially available pharmaceutically acceptable adjuvants are limited, representative examples of adjuvants include Bacille Calmette-Guerin, BCG, or the synthetic adjuvant, QS-21 comprising a homogeneous saponin purified from the bark of *Quillaja saponaria, Corynebacterium parvun*, (McCune et al., 1979, Cancer 43:1619), and IL-12.

Immunogenic compositions comprising immunogens identified according to the invention may be administered to a subject using either a protein or nucleic acid vaccine so as to produce in the subject, an amount of the selected immunogen which is effective in inducing a therapeutic immune response against the target antigen in the subject. The subject may be a human or nonhuman subject. The term "therapeutic immune response", as used herein, refers to an increase in humoral and/or cellular immunity, as measured by standard techniques, which is directed toward the target antigen. Preferably, the induced level of immunity directed toward the target antigen is at least four times, and preferably at least 16 times the level prior to the administration of the immunogen. The immune response may also be measured qualitatively, wherein by means of a suitable in vitro or in vivo assay, an arrest in progression or a remission of a neoplastic or infectious disease in the subject is considered to indicate the induction of a therapeutic immune response.

In the methods of the present invention, a therapeutically effective amount of an immunogen (e.g., a second binding substance) is administered to a mammal in need thereof. The term "administering" as used herein means delivering the antibodies of the present invention to a mammal by any method that may achieve the result sought. They may be administered, for example, intravenously or intramuscularly. The term "mammal" as used herein is intended to include, but is not limited to, humans, laboratory animals, domestic pets and farm animals. "Therapeutically effective amount" means an amount of antibody of the present invention that, when administered to a mammal, is effective in producing the desired therapeutic effect, such as inhibiting kinase activity.

Compositions comprising antigenic peptides of the invention may be administered cutaneously, subcutaneously, intravenously, intramuscularly, parenterally, intrapulmonarily, intravaginally, intrarectally, nasally or topically. The composition may be delivered by injection, orally, by aerosol, or particle bombardment.

Compositions for administration may further include various additional materials, such as a pharmaceutically acceptable carrier. Suitable carriers include any of the standard pharmaceutically accepted carriers, such as phosphate buffered saline solution, water, emulsions such as an oil/water emulsion or a triglyceride emulsion, various types of wetting agents, tablets, coated tablets and capsules. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients. The composition of the invention may also include suitable diluents, preservatives, solubilizers, emulsifiers, adjuvants and/or carriers. Such compositions may be in the foam of liquid or lyophilized or otherwise dried formulations and may include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g. glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexing with metal ions, or incorporation of the material into or onto particulate preparations of polymeric compounds such as polylactic acid, polyglycolic acid, hydrogels, etc. or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

As an alternative to direct administration of a peptide immunogen, one or more polynucleotide constructs may be administered which encode the peptide immunogen in expressible form. The expressible polynucleotide constructs are introduced into cells in the subject using ex vivo or in vivo methods. Suitable methods include injection directly into tissue and tumors, transfecting using liposomes, receptor-mediated endocytosis, particle bombardment-mediated gene transfer, and other methods of gene transfer. The polynucleotide vaccine may also be introduced into suitable cells in vitro which are then introduced into the subject. To construct an expressible polynucleotide, a region encoding the peptide antigen is prepared and inserted into a mammalian expression vector operatively linked to a suitable promoter such as the SV40 promoter, the cytomegalovirus (CMV) promoter, or the Rous sarcoma virus (RSV) promoter. The resulting construct may then be used as a vaccine for genetic immunization. The nucleic acid polymer(s) could also be cloned into a viral vector. Suitable vectors include but are not limited to retroviral vectors, adenovirus vectors, vaccinia virus vectors, pox virus vectors and adenovirus-associated vectors. Specific vectors which are suitable for use in the present invention are pcDNA3 (In-Vitrogen), plasmid AH5 (which contains the SV40 origin and the adenovirus major late promoter), pRC/CMV (InVitrogen), pCMU II (Paabo et al., EMBO J. 5:1921-1927 (1986)), pZip-Neo SV (Cepko et al., Cell 37:1053-1062 (1984)) and pSRα (DNAX, Palo Alto, Calif.).

Throughout this application, various publications, patents, and patent applications have been referred to. The teachings and disclosures of these publications, patents, and patent applications in their entireties are hereby incorporated by reference into this application to more fully describe the state of the art to which the present invention pertains.

It is to be understood and expected that variations in the principles of invention herein disclosed may be made by one skilled in the art and it is intended that such modifications are to be included within the scope of the present invention.

The examples which follow further illustrate the invention, but should not be construed to limit the scope in any way.

EXAMPLES

Example 1

Identification of Prostate Cancer-Specific Antigen and Induction of Immunity

In this example, a prostate cancer specific antigen is first identified by developing a scFv that differentially binds to gp96-antigen complexes from tumor cells and isolating and characterizing the complete protein that comprises the epitope to which the scFv binds. Mimotopes of the prostate specific antigen are obtained by screening for peptides that bind to the same scFv.

With respect to prostate cancer, several cell lines exist having varied biological characteristics with respect to tumorigenic potential, hormone sensitivity and metastatic properties. Dunning G is an androgen sensitive tumor line which is slow growing and possesses no metastatic ability. Dunning H is a heterogenous population of cells, passaged as tumors in castrated rats. Mat-LyLu is a subline of Dunning H which is androgen insensitive, has a short doubling time, and metastasises to the lung and lymph nodes.

A binding protein is developed that is specific for a heat shock protein-peptide complex from Mat-LyLu, but which does not bind to a heat shock protein-peptide complex from normal tissue. First, a library of single chain Fv (scFv) antibodies displayed on phage is panned against gp96-peptide complexes from liver. The library comprises heavy chains encoded by 49 human $V_H$ genes with synthetic D and $J_H$ sequences. Thus, unlike $V_H$-CDR1 and $V_H$-CDR2, which are encoded in the $V_H$ genes, $V_H$-CDR3 is synthetic. As identical light chain is used in all members of the scFv library. Unadsorbed phage are recovered and the panning process is repeated two more times to remove phage that bind to complexes from normal tissue. Unadsorbed phage are then panned over tumor derived heat shock protein-peptide complexes. Adsorbed phage are recovered and amplified.

Three rounds of differential panning are then performed. In each round, amplified phage are first panned over liver derived gp96-peptide complexes. Unadsorbed phage are then panned over tumor-derived gp96-peptide complexes. Adsorbed phage are recovered and amplified.

Adsorbed phage at the last stage of panning are eluted and individual phage clones are tested for reactivity to gp96-peptide complexes by ELISA. Reactivity against both tumor-derived gp96-peptide complexes and normal liver-derived gp96-peptide complexes is determined. The phage recovered in the last step display a significant binding differential. In most cases, binding of the phage clones to liver-derived complexes is not above background.

Phage clones are then tested to determine whether the gp96-peptide complexes to which they bind are tumor specific. ELISA assays are performed using gp96-peptide complexes purified from Mat-LyLu, Dunning G, liver and normal prostate cells. The phage clones are specific for a gp96-peptide complex made by Mat-LyLu cells that is not present in normal cells or in Dunning G.

The heavy chain sequences of two scFvs that bind to tumor derived gp96 complexes are determined. Both have $V_H3$ heavy chains and the same $V_H$-CDR3 sequence (GKYIRSV: SEQ ID NO:4). One of the scFvs (E6) is tested and found to precipitate a 170 kD protein from MAT-LyLu cells. The protein is analyzed for amino acid composition, sequence and cleavage patterns and identified as heavy polypeptide 9 of non-muscle myosin (NCBI Accession #6981236).

Two phage display libraries are panned to identify peptides that bind to MAT-LyLu specific scFv E6. One library comprises 12-mer peptide inserts (the "LX-8 library"), including two cysteine residues and a sulfide bridge. The second library comprises "linear" 15-mer peptide inserts (the "X-15 library").

scFv E6 is biotinylated and bound to streptavidin coated 96 well microtiter plates for 1 hr. at 4° C. The plates are washed and blocked with 300 μl blotto (5% milk, 10 mM EDTA) containing 0.12 mM biotin at room temperature for 2 hr. To each well is added 50 μl blotto and 100 μl TBS containing $10^{12}$ virions. The plates are incubated at for 4 hr. at 4° C. The wells are washed with TBS and bound phage are eluted by adding 35 μl of elution buffer (0.1 M HCl, pH 2.2) and incubating at room temperature for 10 min. Eluted phage are neutralized with 6.6 μl of 1 M Tris, pH 9.1 and amplified using *E. coli* K91. Panning and amplification steps are repeated until four rounds of panning have been performed.

Reactivity of several peptide phage from the X-15 library and the LX-8 library to the scFv is determined by ELISA. Peptides are identified in each library that bind to scFv E6 but not to a control antibody. The amino acid sequence of a peptide from the LX-8 library is YCQEGDAPRLCL ("BTE6-LX-8b"; SEQ ID NO:1). The sequences of two peptides from the X-15 library are determined to be YQPPSDAL-RWILRLQ ("BTE6-X15-4"; SEQ ID NO:2) and GQWQS-GDRYWMETST ("BTE6-X15-7"; SEQ ID NO:3).

A peptide from each of the libraries is synthesized according to the above sequences and conjugated to KLH using 0.25% glutaraldehyde. Copenhagen rats are immunized subcutaneously (day 0) with either peptide (100 µg peptide/animal) in complete Freund's adjuvant (CFA) or 40 µg MLL-derived gp96 in PBS. On day 14, the rats are boosted with 50 µg peptide/animal in incomplete Freund's adjuvant (IFA) or 40 µg MILL-derived gp96 and challenged subcutaneously with 10,000 MAT-LyLu cells/animal. A second boost (50 µg/animal in WA) is administered on day 21.

On day 21, prior to boost, and again on day 28, immunized rats are bled and screened for antibody production by ELISA. Immunization with each of the peptides elicits an immune response that is peptide specific. For example, while BTE6-LX-8b antisera reacts with BTE6-LX-8b peptide, there is no cross-reactivity with BTE6-X15-7 peptide. In contrast, immunization with MLL-derived gp96 does not elicit a measurable immune response.

Two weeks after subcutaneous challenge (day 28), tumors arising from MAT-LyLu cells are evaluated for size. Large masses are found to develop in control rats immunized with MILL-derived gp96. In contrast, there is little, if any, tumor progression in rats immunized with BTE6-LX-8b or BTE6-X15-7.

Example 2

Induction of Immunity Against Multiple and Unspecified Antigens

In this example, mimotopes of mouse mammary tumor specific antigens are sought. No attempt is made to determine the identity of any cancer specific antigen.

A population of binding proteins is developed that binds to hsp-peptide complexes from mammary tumor cells, but not to hsp-peptide complexes from normal mammary tissue. A library of single chain Fv antibodies displayed on phage is panned multiple times against gp96-peptide complexes from diseased and normal tissue according to the protocol of Example 1. Members of the recovered population are tested for binding specificity. Over 90% of the recovered scFv-phage bind specifically for hsp-peptide complexes from breast tumor cells.

As in Example 1, two peptide-phage display libraries are panned to identify peptides that bind to the recovered, amplified population of scFv-phage.

The sequences of ten peptides from each of the libraries are determined, and The peptides are synthesized and conjugated to KLH using 0.25% glutaraldehyde. Mice are immunized sub-cutaneously (day 0) with a mixture of the 20 conjugates (50 µg peptide/animal) in complete Freund's adjuvant (CFA) or a conjugate of a non-specific peptide (control). On day 14, the mice are boosted with 50 µg peptide/animal in incomplete Freund's adjuvant (IFA) and challenged subcutaneously with 10,000 tumor cells/animal. A second boost (50 µg/animal in IFA) is administered on day 21.

Two weeks after subcutaneous challenge (day 28), tumors arising from mammary tumor cells are evaluated for size. Cell masses are found to develop in control rats immunized. In contrast, there is little, if any, tumor progression in rats immunized with the mixture of 20 conjugates.

What is claimed is:

1. A method of making an immunogenic composition against a target cell or an antigen thereof, wherein the target cell is a tumor cell or an infected cell, comprising:
   a) isolating first binding substances that specifically bind to heat shock protein-peptide complexes differentially expressed by the target cell relative to a normal cell, wherein the first binding substances are antibodies or antigen binding fragments thereof;
   b) isolating second binding substances that specifically bind to the first binding substances, wherein the second binding substances are peptides or anti-idiotypic antibodies; and
   c) incorporating the second binding substances into the immunogenic composition.

2. The method of claim 1, wherein the isolated first binding substances are a single species.

3. The method of claim 1, wherein the isolated first binding substances are a mixture of species.

4. The method of claim 1, wherein the second binding substances are a single species.

5. The method of claim 1, wherein the second binding substances are a mixture of species.

6. The method of claim 1, wherein the isolated first binding substances are obtained by screening a phage display library.

7. The method of claim 1, wherein the isolated second binding substances are obtained by screening a phage display library.

8. The method of claim 1, wherein the antigen binding fragments are Fabs.

9. The method of claim 1, wherein the antigen binding fragments are single chain Fvs.

10. The method of claim 1, wherein the isolated second binding substances are peptides.

11. The method of claim 10, wherein the peptides are 30 amino acids or fewer in length.

12. The method of claim 10, wherein the peptides are from 4 to 20 amino acids in length.

13. The method of claim 10, wherein the second binding substances are from 7 to 15 amino acids in length.

14. The method of claim 1, wherein the heat shock protein-peptide complexes comprise complexes of more than one heat shock protein.

15. The method of claim 1, wherein the heat shock protein-peptide complexes comprise a heat shock protein selected from gp96, BiP, hsp70, hsc70, hsp60, hsp40 and hsp90.

16. The method of claim 1, wherein the heat shock protein is gp96.

17. The method of claim 1, wherein the target cell is a tumor cell.

18. The method of claim 17, wherein the tumor cell is from a sarcoma, a lymphoma, a leukemia, a carcinoma, or a melanoma.

19. The method of claim 18, wherein the carcinoma is selected from carcinoma of the breast, carcinoma of the prostate, ovarian carcinoma, carcinoma of the cervix, colon carcinoma, carcinoma of the lung, glioblastoma, and astrocytoma.

20. The method of claim 1, wherein the target cell is an infected cell.

21. The method of claim 20, wherein the infected cell contains a virus, a mycoplasma, a parasite, a protozoan, or a prion.

22. The method of claim 1, wherein in step c) the second binding substances are further conjugated to a carrier.

23. The method of claim 1, wherein in step c) the second binding substances are further complexed with a heat shock protein.

\* \* \* \* \*